United States Patent
Sato

(10) Patent No.: US 7,063,801 B2
(45) Date of Patent: Jun. 20, 2006

(54) COMPOSITE MATERIAL AND METHOD FOR PREPARING THE SAME, AND RAW COMPOSITE MATERIAL USED FOR PREPARING THE SAME

(76) Inventor: Hiroshi Sato, 1-28, Higashihoncho 2-chome, Tendo-City, Yamagata (JP) 994-0000

( * ) Notice: Subject to any disclaimer, the term of this patent is extended or adjusted under 35 U.S.C. 154(b) by 0 days.

(21) Appl. No.: 10/148,990

(22) PCT Filed: Nov. 29, 2000

(86) PCT No.: PCT/JP00/08442

§ 371 (c)(1),
(2), (4) Date: Sep. 17, 2002

(87) PCT Pub. No.: WO01/40399

PCT Pub. Date: Jun. 7, 2001

(65) Prior Publication Data

US 2003/0047027 A1    Mar. 13, 2003

(30) Foreign Application Priority Data

Nov. 30, 1999  (JP)  .................. 11-339232

(51) Int. Cl.
*H01F 1/01* (2006.01)
(52) U.S. Cl. .......... 252/62.51 R; 252/62.55; 252/62.51 C; 252/62.59; 501/126; 501/128; 501/127; 501/129
(58) Field of Classification Search ......... 252/62.51 R, 252/62.51 C, 62.55, 62.59
See application file for complete search history.

(56) References Cited

U.S. PATENT DOCUMENTS

| 4,621,519 | A | * | 11/1986 | Phillips ..................... 73/35.16 |
| 5,769,971 | A | * | 6/1998 | Kuroda et al. .............. 420/434 |
| 5,770,089 | A | * | 6/1998 | Kubo ......................... 210/661 |
| 6,034,013 | A | * | 3/2000 | Kakamu et al. ............. 501/32 |

FOREIGN PATENT DOCUMENTS

| EP | 786785 A1 | | 7/1997 |
| JP | 9-227115 | * | 9/1997 |
| JP | 10-140419 | * | 5/1998 |
| JP | 10-241924 A1 | | 9/1998 |
| JP | 11-165167 A1 | | 6/1999 |
| JP | 2000-264715 | * | 9/2000 |

OTHER PUBLICATIONS

Translation of JP 10-241924.*
Translation of JP 11-165167.*
Defintion of "Tourmaline" from Hawley' Condensed Chemical Dictionary, 14th Ed. 2002.*
Magnetic materials: NDT Resource Center, posted Dec. 25, 2002: www.ndt-ed.org/EducationResources/CommunityCollege/MagParticle.*

* cited by examiner

*Primary Examiner*—C. Melissa Koslow
(74) *Attorney, Agent, or Firm*—Jordan and Hamburg LLP

(57) ABSTRACT

The invention relates to an improvement in tourmaline known as a functional ore. In particular, the invention provides a composite having a novel formation in which a far infrared radiation emitting property and others among tourmaline's properties are effectively exploited, a novel process for producing the composite, and composite materials to be used therefore. The invention includes the composite combining and integrating the tourmaline powder with a magnetizable body so that a laminated or racemic structure is formed, the process for the production of the composite producing a molded body having a racemic structure composed of the tourmaline powder and a magnetizable powder by homogenously mixing and stirring the tourmaline powder with the magnetizable powder, solidifying or freezing by an appropriate means to form a molded body and subsequently magnetizing the magnetizable powder, and a coating liquid form of the composite material composed of the tourmaline and the magnetizable powder to be used for the composite of the invention and the process for the production thereof wherein the tourmaline powder, together with an appropriate adhesive, are homogenously mixed and stirred with the magnetizable powder to form the coating liquid having a racemic structure and finally the magnetizable powder in the coating liquid are magnetized.

17 Claims, No Drawings

COMPOSITE MATERIAL AND METHOD FOR PREPARING THE SAME, AND RAW COMPOSITE MATERIAL USED FOR PREPARING THE SAME

TECHNICAL FIELD

This invention relates to an improvement in tourmaline known as functional mineral ores, and in particular, provides a composite having a new formation by which far infrared ray emission function among their functions can be effectively utilized, a novel process for producing the composite, and composite materials to be used therefore.

BACKGROUND ART

While modern society seems to sing in praise of economic prosperity dependent upon the advances of scientific technology, due to too rapid technical innovation, living environments have become extremely complex and diversified. Suffering from feelings of depression or anxiety that a humanly natural life may not be maintained, individuals have been undergoing stresses, though they are not aware of it and have lived a life with so-called all the modern illnesses such as stiff necks, dizziness, lower back problems, autonomic nerve imbalances and the like. As a result, many people have, in fact, had headaches, insomnia, dizziness, etc. without obvious causes, got easily tired due to gastrointestinal function disorders or stifled, suffered from palpitation or eye fatigue, or experienced abnormal perspiration on the palms of their hands or under their arms.

In addition to these symptoms which can only be attributed to a breakdown in the human psychological balance, in modern societies, in normal daily lives, many people suffer from another physical disorders caused by environments surrounding them.

That is, modern people are concentrated in urban areas, walk on hard-surface roads, and are forced to live in lives surrounded by substances which are sources of positive ions, such as automobiles, electric appliances, buildings of inorganic substances, chemical products such as garments, accessories, etc., and polluted air containing synthetic substances such as toxic gases and so on. Thus, positive ions have been excessively accumulated in human bodies which are apt to lose psychological balance, whereby people must live with predisposed acidity, which is abnormal in nature, for quite a long time.

Originally, normal cells, on cell membranes, retain positive potentials outside cell membranes and negative potentials inside cell membranes, and the negative potential inside of the cell membrane is always maintained higher than the positive potential outside of the cell membrane so as to generate potential differences inside and outside of a cell membrane. This excretes metabolic waste products of a cell and facilitates metabolism in maintaining a healthy body.

But, when the potential balance inside and outside of a cell membrane is, in its environment, disrupted by excessive positive ions, smooth metabolism by the potential differences is inhibited and it results in reduced functions of each cell and abnormal actions in physiological active functions of body. As a result, aging of skin such as rough skin, spots, fine wrinkles, etc. is disadvantageously progressed, or various diseases of internal organs such as hypertension, hypotension, arteriosclerosis, allergy disorders, rheumatoid, nerve pain, cerebral stroke, cardiac disease, cancers and the like are likely to be induced bringing physiological pain.

When all is taken into consideration, it is true that modern people have become exposed to extremely disadvantaged environments both physiologically and psychologically.

Therefore, before singing in praise of affluent lifestyles, it seems necessary for modern people to recognize stress levels accurately and treat stress appropriately in its early stages as well as to suppress occurrence and intake of positive ions into the body and incorporate negative ions actively from outside body, in order to increase negative ions in the body and facilitate metabolism of cells. For such stress control, as psychological treatments, for example, aromatherapy and hot spring therapy which can be taken easily by oneself and rather exclusive therapies such as hypnotic cures have been recognized, and their active exploitation is recommended, while, as physical treatments, herb remedies, acupuncture and cautery remedies, and chiropractics, etc. which are folk remedies have been popular. Magnetic remedies which can be taken daily and easily to help physical conditions improve is also used by many as a promising means to overcome modern diseases for themselves.

For utilizing the functions of magnetic field lines of magnets, a magnetic treatment apparatus was officially registered as a treatment apparatus by the Pharmaceutical Affairs Law of 1961. When the human body is magnetically affected, ionization into positive and negative ions in blood is affected by of "Fleming's Left-Hand Rule" induced by a magnetic field. Such a force activates flows of those ions in blood. As a result, blood flow containing those ions is also activated to help improve various conditions attributed to failures in blood flow such as stiff necks, dizziness, lower back problems, autonomic ataxia and the like, and this mechanism has been officially authorized. Subsequently, the magnetic treatment apparatus have been widely distributed and accepted as a completely harmless treatment apparatus utilizing natural energy, especially as a magnetic band, magnetic necklace and the like.

With such a trend, over 10 years ago when high power magnets, or "rare earth magnets", which have high power magnetic energy, such as "samarium cobalt magnet" of which magnetic energy is 2000 gauss oersted (approx. 5 folds of ferrite magnet) and "alnico magnet" which has a 30-fold-power of casting magnets were developed, it became possible to downsize the magnetic treatment apparatus. Thus, a magnetic patch chip at one point which can carry out treatment in a smart manner (trade names are Pippu Erekiban, etc.) and magnetic necklaces excellent in design have appeared and have given rise to a boom in magnetic treatment apparatuses. At present, the trend has continued to expand.

There have been attempts to improve or overcome physical ailments of modern people such as stiff necks, dizziness, lower back problems, autonomic ataxia and the like by exploiting functions and energy present in the natural world, besides the above-mentioned magnetic force of magnets. In such attempts, a proposal exists to improve physical conditions by continuously drinking natural water ionized through various means, alkali water, and an attempt also exists to supply calcium ingredients to the body for alkalizing the constitution by ingesting the calcium ingredients which are purified by separating pure natural calcium ingredients from Ca compounds present in the natural world such as in shells and corals, and recently, tourmaline has been recognized as a new natural material to achieve such aims, and that in a partially practical phase has been reported.

Tourmaline belongs to hexagonal rhombohedron hemihedral crystalloid, and most are composed of columnar crystals. It is an ore of which the column surface has remarkable vertical lines. Its hardness is 7 to 7.5 and specific gravity is 3 to 3.3. Its composition is represented as XY9B3Si6O27 (wherein X is Ca, Na, K or Mn, and Y is Mg, Fe, Cr, Mn, Ti or Li). If containing much iron it exhibits a black color, and if containing less or no iron it exhibits white, blue, green, red, rouge, brown or colorless depending on its components. Among them, the most expensive called Brazil ruby is rouge in color, and one called water melon exhibits green at its crystal periphery and pink inside. These have been prized as jewels and known as noble tourmalines.

However, after piezoelectricity was found by Pierre Currie in 1880, tourmaline has been recognized as a specific mineral matter. Its several specific functions such as emitting negative ions and far infrared rays have been known. Recently, the functions of the tourmaline other than piezoelectricity have been just recognized, and studies on their practical applications are about to begin. An attempt has been proposed in which cells are activated by absorbing negative ions from pressure points of the body to induce in vivo electric current using the negative ion emitting function of tourmaline. Other trials have been reported in which, using the far infrared radiation function of tourmaline, capillary blood vessels are dilated by far infrared rays emitted in receiving heat of body temperature to facilitate peripheral blood flow in order to assist metabolism, improvement of physical conditions and fatigue recovery.

The present inventor whose occupation is total body treatment practice has noticed natural energy in the natural world and has had a great interest in the above-mentioned tourmaline in conjunction with actively exploiting various natural sources The inventor has not only collected and researched data already reported on various properties of tourmaline but also studied further and analyzed them for a long time. While the magnet has been granted a status as an authorized treatment apparatus and solely been used anticipating just a facilitative effect on blood circulation by dynamic action of "Fleming's Left Hand Rule" upon blood in the magnetic field of magnetic field lines, the inventor has found the fact that a specific phenomenon which had never been observed is induced on the functional properties of tourmaline such as semipermanent emission of negative ions, far infrared rays and faint light static flows in response to light, temperature, pressure and friction by combining tourmaline with the magnet, and, based on it, has performed numerous trials and attempts of experiment. As a result, the inventor has succeeded in producing extremely novel composites which combine tourmaline with the magnet and in completing and establishing processes for the production thereof. The formation is described in detail below.

DISCLOSURE OF THE INVENTION

A composite of the invention basically consists of the following formation.

That is, the composite is integrated so that tourmaline powder is combined with a magnetic material in a laminated or racemic structure.

If the formation of the composite having this basic formation is represented in other words, it can be said that the composite has a formation wherein the tourmaline powder is combined with the magnetic material in a laminated or racemic structure to be integrated, and far infrared rays of the tourmaline are elicited by an electromagnetic induction, whereby a temperature elevation of approx. 1° C. above the natural temperature is realized.

The composites having the above-mentioned basic formation include composites having the following formations.

An composite is obtained by integrating the tourmaline powder as a coating layer with the surface of the magnetic material and forming a molded body having a laminated structure composed of tourmaline and the magnetic body, and the composite is obtained by mixing and stirring the tourmaline powder with the magnetic powder, solidifying or freezing by an appropriate means to form a molded body having a racemic structure composed of tourmaline and the magnetic body.

Likewise, there includes any composites wherein the tourmaline powder, together with a clay body, are mixed and stirred with the magnetic-powder to mold into an appropriate shape, which is solidified or frozen by sintering or naturally drying to form a molded body having a racemic structure composed of tourmaline and the magnetic body having a desired shape, and, as composites of this formation, there includes any composites wherein the tourmaline powder, together with the clay body and a silica sol solution, are mixed and stirred with magnetic powder to mold into an appropriate shape, which is frozen by naturally drying to form a molded body having a racemic structure composed of tourmaline and the magnetic body, and any composite wherein the tourmaline powder, together with the clay body and the silica sol solution, are mixed and stirred with the magnetic powder to mold into an appropriate shape, which is frozen by naturally drying and subsequently is solidified by sintering to form a molded body having a racemic structure composed of tourmaline and the magnetic body.

Tourmalines for the tourmaline powder are produced mainly in Brazil (approx. 90% of total production), and also in India, China, Africa, and other countries including Japan. Black or brown tourmalines are produced relatively in abundance, obtained easily, and employed advantageously in powder form of particle size 1 to 200 µm or less, preferably approx. 1 to 50 µm by an appropriate means such as a vibrating mill and so on.

On the other hand, the magnetic body or magnetic powder to combine with the above-mentioned tourmaline is not especially limited and, depending on purposes and usage, Cr magnets, Mg magnets, high power samarium cobalt magnets, alnico magnets and the like, besides the most popular ferrite magnets, can be appropriately employed. As the structure to combine with the above-mentioned tourmaline, the magnetic material is flat or lump, and the surface of that is coated or statically painted with the tourmaline powder, or done so by another means, to integrate for forming the laminated structure. Or, the magnets are made into powder having similar particle size to those of tourmaline, and then both are stirred and mixed together thoroughly to take on a racemic structure, molded into an appropriate shape with various adhesives known in the art, and solidified or frozen.

When the magnetic body which has already been magnetized and provided with a given magnetic force is directly combined with tourmaline, a magnetic force exceeding 3000 gauss, as a rough standard, may lead to disturbing the laminate or mixture of both. Specifically, the tourmaline powder is prone to be repelled, and thus it is necessary that the magnetizable magnetic body is handled to be intact, and the magnetizable magnetic body in the laminated or racemic structure, after being appropriately solidified or frozen, needs to be magnetized by a means of magnetizing the whole. In particular, this is effective in the case of obtaining a composite having a racemic structure.

The clay can be added as a binder in the case of a composite having a racemic structure composed of the tourmaline powder and magnetic powder. Moreover, when a special functional solidification is prepared for the purpose of providing a catalyst function or far infrared effects, a zeolite or silica sol $SiO_2$ solution can be added thereto and dried at room temperature to make a solidification. For the silica sol $SiO_2$ solution, an ultra fine particle solution with, approx. 10 angstrom is desirable as it also holds absorptive properties, ion exchanging ability and bactericidal properties.

It is possible to make the above-mentioned frozen composite a sintered body by sintering. When sintering, zeolite is in a melting state at 850° C. However, in the case of silica sol, in order to retain its functionality, normal temperatures to 300° C. must be kept for the non-crystal, 300 to 550° C. in a sub-stable phase and 550° C. or more in a stable phase. Accordingly, the sintering body must be formed at around a glass transfer temperature Tg 420° C. so as to assure functionality while avoiding damage to end parts of the crystal. In the case of 550° C. or more, parts of silica sol assemble to the surface and a cementite crystal body is readily formed. At that time, if natural drying during mixing is carried out thoroughly, the stable composite can be readily achieved.

Relevant Invention 1

In relation to the composite of the invention having the above-mentioned formation, the invention also includes a process for producing the composite having the following novel formations.

That is, a process for the production of the composite producing the molded body having a racemic structure composed of the tourmaline powder and magnetic powder by homogenously mixing and stirring the tourmaline powder with the magnetizable powder and solidifying or freezing by an appropriate means to form a molded body, followed by magnetizing the magnetizable powder.

Relevant Invention 2

Further, there also includes a process for the production of the composite, wherein a composite material layer having a racemic structure composed of the tourmaline powder and magnetic powder appropriately on the surface of the base substance is formed, by homogenously mixing and stirring the tourmaline powder, together with an appropriate adhesive, with the magnetizable powder to form a coating liquid having a racemic structure, which is coated on the desired surface of the base substance, then drying and solidifying to make a coating layer having a racemic structure on the base substance surface, and subsequently magnetizing the magnetizable powder in the coating layer.

Relevant Invention 3

And, there also includes a process for the production of the composite, wherein a liquid composite material having a racemic structure composed of the tourmaline powder and magnetic powder is produced, by homogenously mixing and stirring the tourmaline powder, together with an appropriate adhesive, with the magnetizable powder to form a coating solution having a racemic structure and subsequently magnetizing the magnetizable powder at 3000 gauss or less in the coating layer.

In any of the above-mentioned processes for the production, the composite having a final homogenous combination structure can be assuredly produced using the tourmaline powder regardless of magnetic force of the magnetic powder in producing a composite having a racemic structure. In particular, in the case of obtaining a composite having a combination structure with the magnetic body having a magnetic force of 3000 gauss or more, it is extremely important that the magnetizable powder is used and that a step to magnetize the magnetizable powder is taken in the final stage.

Relevant Invention 4

Moreover, for the invention, the composite materials are included as materials indispensable for the above-mentioned composites and the process for the production thereof. One of the composite materials is in a coating liquid form composed of the tourmaline powder and magnetizable powder, wherein the tourmaline powder is mixed and stirred, together with an appropriate adhesive, with the magnetizable powder to form the coating liquid having a racemic structure and the magnetizable powder is finally magnetized in the coating layer.

Relevant Invention 5

And, the other composite material is a powdery composite material composed of the tourmaline powder and magnetizable powder, wherein a racemic structure is formed only by homogenously mixing and stirring the tourmaline powder and magnetizable powder of particle size 1 to 200 μm, preferably 1 to 50 μm, and the magnetizable powder is finally magnetized.

In the case of a composite material which is a coating liquid form, it is possible to make such composite material capable of being applied to any base substances by combining with additives or coating materials as solvents of optimal types and characteristics for such base substances. In particular, it can be used as an adhesive or coating film formation on the surface or between the non-magnetic bodies such as leathers, synthetic resin plates or sheets, ceramic wares, glasses, non-magnetic metals such as aluminium etc., woods and the like. Thus, the composite layer of the invention can be formed not only on the surfaces and inside of personal equipment and goods but also on the appropriate site of various mechanical instruments and building materials. If the composite material is magnetized in the final stage, the formation of the composite layer of the invention is possible, and even demagnetization is possible by conducting a converse manipulation.

In the case of a composite material which is, powdery, the composite material plays a role as a base material for composites of the invention and the process for the production thereof as well as the above-mentioned composite material which is a coating liquid. If it is added into the adhesive or coating material, it becomes the composite material which is in a coating liquid form. Or uses in various forms are possible such as dispersal use to the adhesive or the coating surface, in addition to plastic materials and the like. As is the case with the above-mentioned coating liquid form, the step of magnetizing is required in the final stage.

BEST MODE FOR CARRYING OUT THE INVENTION

The representative examples are illustrated below so as to further clarify the above-mentioned formations of the invention.

Example 1

A ferrite magnet (9 g) is roughly crushed, mixed with an equivalent amount of gray tourmaline, and then crushed in a vibrating mill for 5 minutes to make fine powder of particle size 5 μm or less. The fine powder is a composite material as brown powder with the color tone close to chocolate.

The composite material was measured for emission of far infrared rays of 3 to 19 m wavelength using a radiation thermometer, "IR-TE MT1000 (Yamagata Chino)" (accuracy at the calibration point). For a comparison control, simple tourmaline powder having the same particle size was also measured under the same conditions.

The results of the 10 scannings for each areas shown in the following Table 1. It was demonstrated that the temperature of the composite material was 0.31° C. higher on average than that of the simple tourmaline.

TABLE 1

| Type of sample | Integrated total temperature* | Average temperature | Difference in temperature |
| --- | --- | --- | --- |
| Composite of tourmaline powder and magnetic powder | 245.8 | 24.58 | |
| Simple tourmaline powder | 242.7 | 24.27 | 0.31 |

*The integrated total is the total value of 10 scannings for each sample.

Example 2

Next, a magnet of 640 gauss was placed on the composite material of the Example 1 above and magnetic induction was carried out for 2 min. Subsequently, the temperature difference was measured, comparing with the sample without magnetic induction.

The results of 7 scannings for each are as shown in Table 2. It was found that the temperature of the composite material with magnetic induction was 1.08° C. higher on average compared to that of composite material without magnetic induction. This means 1.39° C. higher on average compared to the simple tourmaline in said Example 1.

The measuring apparatus and numeric processing are the same as the case 10 with said Example 1.

TABLE 2

| Type of sample | Integrated total temperature* | Average temperature | Difference in temperature |
| --- | --- | --- | --- |
| Composite with magnetic induction | 179.7 | 25.67 | |
| Composite without magnetic induction | 172.1 | 24.58 | 1.08 |

*The integrated total is the total value of 7 scannings for each sample.

INDUSTRIAL APPLICABILITY

An established fact that the composite of the invention having the above mentioned formation had a very warm effective temperature was obtained as a result of monitoring 75 people who wore leather shoes of which insoles contained 1 g of the composite with magnetic induction as in Example 2. As for a composite having a laminated or racemic structure composed of tourmaline powder and magnetic powder, it is believed that the crystal structure of tourmaline which is proximally disposed causes distortion by electron orbit kinetic energy, which involves magnetism when electrons are incorporated from an atmosphere, and it results in emitting far infrared rays and leads to a slight temperature elevation as the entire composite. This phenomenon has never been reported. It is an effect which cannot be obtained from either the magnet alone or the tourmaline alone. The synergistic effect obtained from the combination thereof is immeasurable.

Furthermore, even when integrated into the composite, the tourmaline powder, the magnetic body and magnetic powder never lose their own properties. Original actions of the tourmaline are retained such as the far infrared ray effect, action to water surface tension, bactericidal action, deodorant action and the like. The magnetic body remains to possess growth facilitating action to plants, facilitating actions to enzymatic reactions, control and bactericidal action for microbes, blood flow facilitating action and the like. Additionally, the characteristics that these action effects are obtained solely or synergistically can be also gained. The composite has an advantage that it is capable of being exploited instead for various fields where those are used solely.

In the process for the production of the composite, by employing a process in which a magnetizable body is combined with the tourmaline powder and magnetization is carried out in the final stage to produce the desired composite, especially, the combination of a high power magnetic body with the tourmaline powder can be ideally carried out. Therefore, the resultant composite covers a broad application range such as daily personal equipment and goods, special treatment instruments, cultivation instruments, measuring instruments, building materials and the like for culture of life, agriculture, industries, medicine, academic research and the like. In particular, the coating liquid form of the composite material having a combination of tourmaline powder and magnetizable powder can be highly promising for a broad application range.

As mentioned above, the composite, the process for the production thereof and the composite material of the invention can widely achieve the desired objectives by their novel formations and are anticipated to be highly evaluated in various fields, and widely distributed and utilized.

What is claimed is:

1. A composite wherein a tourmaline powder is mixed and stirred, together with a clay body and a silica sol solution, with a magnetic powder to mold into an appropriate shape and subsequently frozen by natural drying to form a molded body having a racemic structure composed of tourmaline and the magnetic body.

2. A composite wherein a tourmaline powder is mixed and stirred, together with a clay body and a silica sol solution, with a magnetic powder to form a mixture, which is molded into an appropriate shape and is subsequently frozen by natural drying, then sintered and solidified to form a molded body having a racemic structure composed of tourmaline and the magnetic body.

3. Composite comprising a tourmaline powder, with a hexagonal rhombohedron hemihedral crystalloid crystallographic structure, said powder having a particle size of 1 μm to 200 μm, said powder being integrated with a surface of a magnetizable body made of a magnetizable substance selected from the group consisting of chromium (Cr), samarium cobalt (SmCo), alnico (AlNiCo), and ferrite, with said powder and said magnetizable body being formed into a hardened molded body having a laminar structure of said tourmaline powder as a coating layer on said magnetizable body; and wherein said magnetizable substance of said magnetizable body has been magnetized after said coating layer has been applied.

4. Composite comprising a tourmaline powder, with a hexagonal rhombohedron hemihedral crystalloid crystallographic structure, said tourmaline powder having a particle size of 1 µm to 200 µm, mixed and stirred with a magnetizable powder selected from the group consisting of chromium (Cr), samarium cobalt (SmCo), alnico (AlNiCo), and ferrite, having a particle size of 1 µm to 200 µm, and a clay, and formed into a molded body, which has been solidified and hardened by sintering or drying, and which has a homogenous composition or said tourmaline powder, said magnetizable powder, and said clay; and wherein said magnetizable powder has been magnetized after formation of said molded body.

5. Composite comprising a tourmaline powder, with a hexagonal rhombohedron hemihedral crystalloid crystallographic structure, said tourmaline powder having a particle size of 1 µm to 200 µm, mixed and stirred with a magnetizable powder, selected from the group consisting of chromium (Cr), samarium cobalt (SmCo), alnico (AlNiCo), and ferrite, having a particle size of 1 µm to 200 µm, a clay, and a silica sol or a zeolite, and formed into a molded body, which has been solidified and hardened by drying, and which has a homogenous composition of said tourmaline powder, said magnetizable powder, said clay, and said at least one of a silica sol and a zeolite; and wherein said magnetizable powder has been magnetized after formation of said molded body.

6. Process for production of a composite of a tourmaline powder and a magnetizable powder, said process comprising:
   homogeneously mixing and stirring a tourmaline powder, with a hexagonal rhombohedron hemihedral crystalloid crystallographic structure, said tourmaline powder having a particle size of 1 µm to 200 µm, with a magnetizable powder of a magnetizable substance selected from the group consisting of chromium (Cr), samarium cobalt (SmCo), alnico (AlNiCo), and ferrite, having a particle size of 1 µm to 200 µm;
   forming a molded body from said homogeneously mixed tourmaline powder and said magnetizable powder;
   solidifying and hardening said molded body; and
   magnetizing said magnetizable powder in said molded body.

7. Process for production of a liquid coating form of a homogeneously blended composite of a tourmaline powder and a magnetizable powder, on a base substance surface, said process comprising:
   homogeneously mixing and stirring a tourmaline powder, with a hexagonal rhombohedron hemihedral crystalloid crystallographic structure, said tourmaline powder having a particle size of 1 µm to 200 µm, with a magnetizable powder of a magnetizable substance selected from the group consisting of chromium (Cr), samarium cobalt (SmCo), alnico (AlNiCo), and ferrite, having a particle size of 1 µm to 200 µm, and a liquid adhesive, to form a coating liquid having a homogenous structure;
   coating said coating liquid on said base substance surface;
   drying and solidifying said coating liquid on said base substance surface to form a dried coating layer, having a homogenous structure, on said base substance surface; and
   magnetizing said magnetizable powder in said dried coating layer.

8. Process for production of a liquid composite of a tourmaline powder, with a hexagonal rhombohedron hemihedral crystalloid crystallographic structure, said tourmaline powder having a particle size of 1 µm to 200 µm and a magnetizable powder, of a magnetizable substance selected from the group consisting of chromium (Cr), samarium cobalt (SmCo), alnico (AlNiCo), and ferrite, having a particle size of 1 µm to 200 µm, to form a composite having a homogenous structure, said process comprising:
   homogeneously mixing and stirring said tourmaline powder with said magnetizable powder and a liquid adhesive, to form a homogenous liquid coating;
   applying said liquid coating to a base substance surface and drying said liquid coating to form a coating layer on said base substance surface; and
   magnetizing said magnetizable powder in said coating layer, by exposing said magnetizable powder in said coating layer to a magnetic field not in excess of 3000 gauss.

9. Coating liquid form of a composite material comprising at least a tourmaline powder and a magnetizable powder; and
   an adhesive,
   said tourmaline powder and said adhesive being homogeneously mixed with said magnetizable powder to form said coating liquid.

10. Coating liquid form of composite material, according to claim 9, wherein said magnetizable powder in said coating liquid is magnetized after being homogeneously mixed.

11. Process for the production of a coating liquid form of a composite material, comprising the steps of:
   forming a homogenous mixture of a tourmaline powder and an adhesive to form a homogenous mixture;
   performing at least one of mixing and stirring said mixture with a magnetizable powder to form said coating liquid; and
   magnetizing said magnetizable powder.

12. Process for the production of a coating liquid form of a composite material, comprising the steps of:
   mixing and stirring a tourmaline powder, a liquid adhesive, and a magnetizable powder to form a homogenous mixture; and
   magnetizing said magnetizable powder.

13. Process for the production of powder composite material comprising the steps of:
   homogeneously mixing and stirring a tourmaline powder and a magnetizable powder;
   said tourmaline powder and said magnetizable powder having particle sizes from about 1 to 200 µm; and
   magnetizing said magnetizable powder.

14. Process for the production of powder composite material, according to claim 13, wherein said particle sizes are from 1 to 50 µm.

15. Process for the production of powder composite material, according to claim 13, wherein said step of homogeneously mixing and stirring includes a step of adding at least one of a clay and a silica sol solution.

16. Composite substance comprising:
   first particles of a tourmaline powder with a hexagonal rhombohedron hemihedral crystalloid crystallographic structure, said first particles having a particle size of 1 µm to 200 µm;
   second particles of a magnetizable substance, capable of being magnetized, said second particles being selected from the group consisting of chromium (Cr), magnesium (Mg), samarium cobalt (SmCo), alnico (AlNiCo), and ferrite, and having a particle size of 1 μm to 200; and a clay.

17. Composite substance comprising:

first particles of a tourmaline powder with a hexagonal rhombohedron hemihedral crystalloid crystallographic structure, said first particles having a particle size of 1 μm to 200 μm;

second particles of a magnetizable substance, capable of being magnetized, said second particles being selected from the group consisting of chromium (Cr), samarium cobalt (SmCo), alnico (AlNiCo), and ferrite, and having a particle size of 1 μm to 200 μm; and a zeolite or a silica sol.

* * * * *